United States Patent
Schimmelpfennig et al.

(10) Patent No.: US 6,508,943 B2
(45) Date of Patent: Jan. 21, 2003

(54) FILTERING DEVICE AND A FILTERING METHOD

(75) Inventors: Winfried Schimmelpfennig, Cracow (DE); Holger Lantow, Rostock (DE); Uwe Müller, Nuremberg (DE); Wilfried Riggers, Bremerfoerde (DE)

(73) Assignee: Plasmaselect Aktiengesellschaft, Teterow (DE)

( * ) Notice: Subject to any disclaimer, the term of this patent is extended or adjusted under 35 U.S.C. 154(b) by 38 days.

(21) Appl. No.: 09/774,642

(22) Filed: Feb. 1, 2001

(65) Prior Publication Data
US 2001/0032811 A1 Oct. 25, 2001

Related U.S. Application Data

(63) Continuation of application No. PCT/EP99/04554, filed on Jul. 1, 1999.

(30) Foreign Application Priority Data

Aug. 3, 1998 (DE) .......................... 198 34 915
Nov. 13, 1998 (DE) .......................... 198 52 466

(51) Int. Cl.⁷ .............................................. B01D 63/16
(52) U.S. Cl. ............ 210/780; 210/321.63; 210/321.67; 210/321.68; 210/321.76; 210/321.85; 210/330; 210/332
(58) Field of Search .................... 210/780, 321.63, 210/321.67, 321.68, 321.76, 321.85, 330, 332

(56) References Cited

U.S. PATENT DOCUMENTS 5,034,135 A * 7/1991 Fischel .................. 210/321.68

FOREIGN PATENT DOCUMENTS

| EP | 238 335 A | 9/1987 |
| JP | 01 155266 A | 6/1989 |
| WO | WO 90/00069 A | 1/1990 |
| WO | WO 97/19745 A | 6/1997 |

OTHER PUBLICATIONS

PTO 02–2225; Translation of JP 01–155266 which was published on Jun. 19, 1989.*

* cited by examiner

*Primary Examiner*—David A. Reifsnyder
(74) *Attorney, Agent, or Firm*—Lawrence E. Laubscher, Sr.

(57) ABSTRACT

The present invention refers to a filtering device comprising at least one filtering membrane, at least one counter surface opposite to the filtering membrane, and at least one gap-shaped liquid space formed between the filtering membrane and the counter surface. The present invention further refers to a filtering method, in which a liquid is introduced into a gap-shaped liquid space formed between a filtering membrane and a counter surface and is moved relative to the filtering membrane and/or the counter surface. To obtain an improved filtering method and an improved filtering device, it is suggested by the present invention that the filtering device comprises a disk at whose circular surface at least the filtering membrane or the counter surface is formed. In the method according to the invention, two helical liquid whirls are generated in the gap-shaped liquid space, said whirls extending in parallel to the filtering membrane and the counter surface and having the same sense of rotation but opposite radial directions of movement.

8 Claims, 3 Drawing Sheets

FILTERING DEVICE AND A FILTERING METHOD

REFERENCE TO RELATED APPLICATION

This is a continuation application of PCT Application No. PCT/EP99/04554 filed Jul. 1, 1999.

BACKGROUND OF THE INVENTION

1. Field of the Invention

The present invention refers to a filtering device comprising at least one filtering membrane, at least one counter surface opposite to the filtering membrane and at least one gap-shaped liquid space formed between the filtering membrane and the counter surface. The present invention further refers to a filtering method, in which a liquid is introduced into a liquid space formed between a filtering membrane and a counter surface, said liquid being moved relative to the filtering membrane and/or counter surface.

2. Description of Detailed Art

A device and a method comprising the above-mentioned features are known from U.S. Pat. No. 5,034,135. By means of this known prior art, a liquid to be filtered is introduced into a cylindrical annular gap, which extends between a stationary outer cylinder which forms the counter surface and a rotating filtering cylinder at which the filtering membrane is arranged. This device is in particular suitable for filtering blood to separate the components blood plasma on the one hand and blood cells on the other hand from one another. U.S. Pat. No. 5,034,135 teaches that an outwardly directed centrifugal force is generated by the rotating filtering cylinder, said centrifugal force forcing the blood cells from the membrane outwardly whereas at the same time the blood plasma is separated from the blood cells due to a trans-membrane pressure acting through the filtering membrane. The filtrate (blood plasma) generated thereby is radially guided inwardly in the filter and is continuously guided outwardly via a rotary seal arranged in the center of rotation of the filtering cylinder.

The known device is superior to conventional filtering devices in which a suspension or an emulsion is split up at a micro-porous membrane exclusively on the basis of the trans-membrane pressure into filtrate on the one hand and into concentrate on the other hand, since by the rotation of the filtering cylinder, a motion of the liquid relative to the filtering membrane is generated and thereby a clogging of the filtering pores by the solid matter or cells or emulgated droplets is prevented. The disadvantage of the known device is, however, that it is relatively voluminous. Moreover, the structure of the known device requires a relatively high constructive effort. This in particular applies for the rotary seal, which can moreover also lead to a leakage. In particular when filtering blood, the problem of a safe and reliable sealing further occurs.

SUMMARY OF THE INVENTION

It is the object of the present invention to provide an improved filtering method and an improved filtering device. In particular, it is the object of the present invention to provide a filtering device in which a clogging of the filtering pores is prevented, which requires few space and which can be manufactured in an especially simple and inexpensive manner.

To solve the above-mentioned object by means of an apparatus, the above-mentioned filtering device is developed according to the invention in that at least the filtering membrane or the counter surface are formed as a surface of a rotary body, which is substantially arranged at a right angle with respect to the axis of rotation of the rotary body. Since either the filtering membrane or the counter surface is provided at a rotary body in the filtering device according to the invention, a gap-shaped liquid space is formed between the filtering membrane and the counter surface. If desired, the filtering membrane as well as the counter surface can be formed at one rotary body each. Due to the rotary support of the filtering membrane and/or the counter surface, a relative motion of the liquid to be filtered in the gap-shaped liquid space can be effected to generate micro-whirls at the filtering surface which prevent a clogging of the filtering pores by solid matter, corpusculary particles etc. It has shown that in case of a circular relative motion between the filtering membrane and the counter surface in a circular disk-shaped gap, a macro-flow with two helically extending liquid whirls are formed, extending one above the other and having the same sense of rotation, which, however, have an opposing radial moving direction component. Accordingly, the liquid to be filtered flows helically inwards in the one liquid whirl and helically outwardly in the other liquid whirl. By this mechanism, an aimed macro-flow can be achieved in the gap-shaped liquid space, which has an advantageous effect on the filtering processes.

Since the liquid space extends in parallel to the surface of a rotary body, which is arranged substantially perpendicular to the axis of rotation of the rotary body, the filtering device according to the invention can be realized in a relatively space-saving manner at a relatively large surface compared to the known drum arrangement. The stationary arrangement of the filtering membrane is especially preferred, so that a rotary seal for discharging the filtrate from the device can be dispensed with, which is necessary and disadvantageous in the above discussed structure of the filtering device of the prior art. Thereby the constructive structure of the filtering device according to the invention is especially simplified with respect to the above-discussed prior art.

The rotary body of the filtering device according to the invention has an essentially larger radial than axial extension and is preferably formed by a disk, in particular a circular disk. The surface may be planar or structured to enhance the generation of micro-whirls. In view of an inexpensive and simple manufacture, it is preferred to form the rotary body as a planar disk. As an alternative, the disk can also for instance have a conical or a truncated conical cross section.

A filtering device that has an increased active area at an almost unchanged constructive effort can be obtained in that two opposite filtering membranes are provided between which a circular disk is rotatably supported, each forming a counter surface to the two filtering membranes. In this preferred embodiment, not only the stationary arrangement of the filtering elements leads to a constructive simplification but also the fact that both circular surfaces of the disk are used as counter surfaces.

In a further preferred embodiment of the present invention which is in particular suitable for the filtration of toxic substances or of blood or other body liquids, the rotary body is driveable in a contact-less manner. Accordingly, a shaft penetrating the housing of the filtering device and fixed with the disk for co-rotation can be dispensed with. Rather, the housing is sealed towards the outside in the area of the support of the shaft, so that an emerging, e.g. of toxic liquid, or a penetration of germs or bacterial into the liquid space is safely prevented. A rotary body is especially to be preferred for a contact-less drive, said rotary body being metallically conductive so that the drive is effected by means of magnetic induction by means of an outwardly introduced rotating magnetic field. An exchange of used up filtering devices and a coupling with the drive for the rotatably supported rotary body can therefore be carried out in a simple manner.

BRIEF DESCRIPTION OF THE DRAWING

Further details, features and advantages of the present invention can be derived from the following description of embodiments of the present invention in connection with the enclosed drawing, in which.

DETAILED DESCRIPTION OF THE PREFERRED EMBODIMENT

Figure 1:
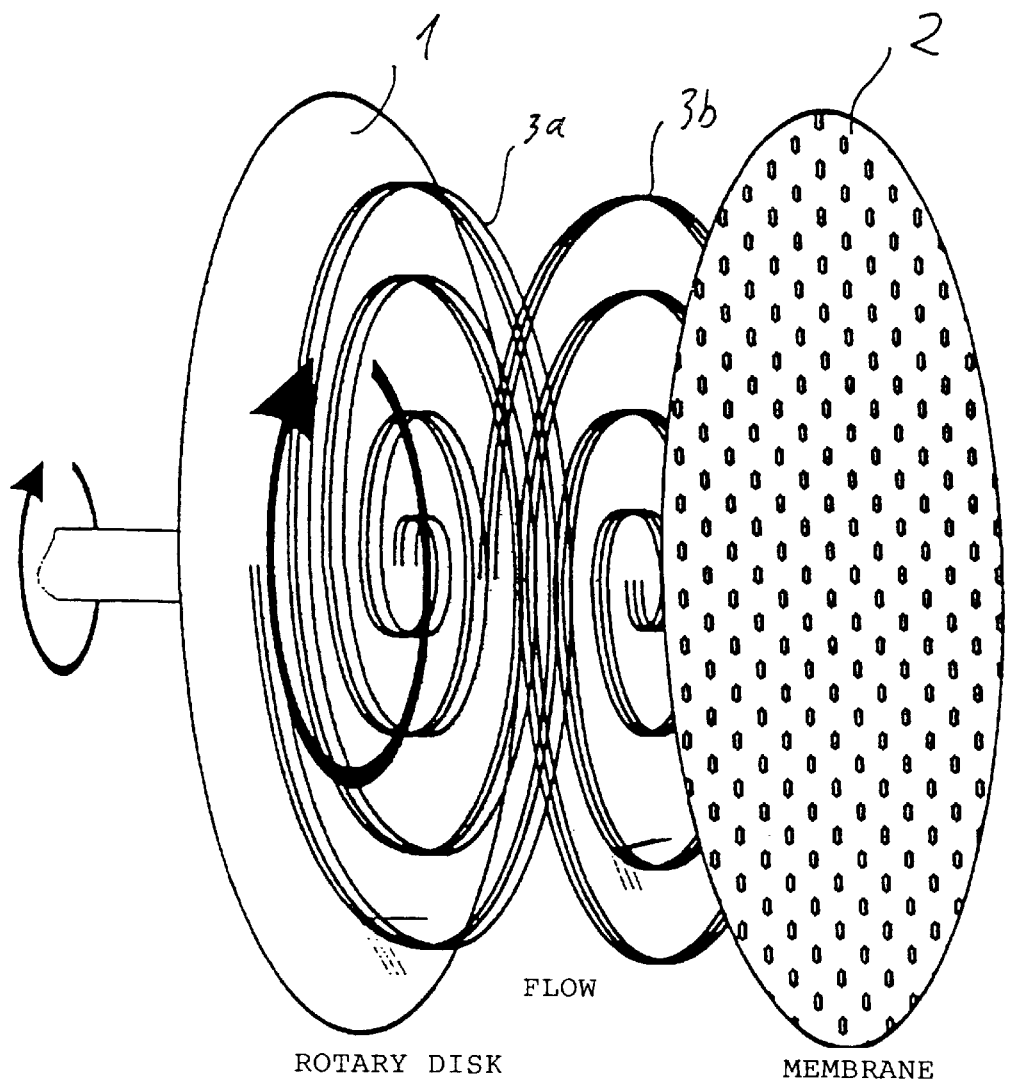
FIG. 1 shows a schematic view of the macro-flow generated in the gap-shaped liquid space.

FIG. 1 shows a schematic view of essential parts of an embodiment of the present invention, which comprises a rotating disk 1 and a stationary membrane 2. The flow generated in the stationary condition, i.e. during constant rotation of the disk, comprises on the one hand a helical liquid whirl 3a effected by the rotation of the disk 1, said liquid whirl extending in parallel to the circular face of the disk 1 and which is formed adjacent to the disk 1. Adjacent to the membrane 2 a whirl 3b is also generated due to the shearing forces generated by the rotation of the disk 1. The whirl 3a and the whirl 3b have the same sense of rotation. The helical liquid whirl 3a generated adjacent to the disk does, however, has an outwardly directed radial speed component, whereas the helical liquid whirl 3b arranged adjacent to the membrane 2 has a radially inwardly directed speed component.

The liquid introduced into a helical liquid space 12 arranged between the disk 1 and the membrane 2 first of all moves over the liquid whirl 3b along the membrane 2 and in the sense of rotation of the disk 1 radially inwardly, until it approximately reaches the center of the disk 1, and then it is transferred to the second helical liquid whirl 3a, which guides the concentrate radially outwardly in a helical movement in parallel to the disk 1. Micro-whirls in particular generated in the proximity of the membrane 2 to prevent a clogging of same, can in particular be influenced by adjusting the distance between the disk 1 and the membrane 2 and by adjusting the speed of the disk 1. The centrifugal force in the rotating liquid generated by rotation of the disk 1 does not contribute to the separation of the particles contained in the liquid, since the centrifugal force only acts in parallel to the surface of the membrane 2 or of the disk 1, respectively. The formation of the macro-whirls in the gap-shaped liquid space is influenced by two essential magnitudes. This is on the one hand the shearing force between the driven surface of the disk 1 and the present stationary surface of the membrane 2, through which the liquid is moved in the tangential direction. On the other hand, the centrifugal force forces the liquid out of the gap. Since this force is greater in the proximity of the rotating disk than in the proximity of the stationary membrane, an aimed discharge of concentrate through the helical liquid whirl 3a results due to the superposition of shearing force on the one hand and centrifugal force on the other hand, whereas liquid is taken in through the counter-whirl 3b as a result of the volume constancy.

Figure 2:
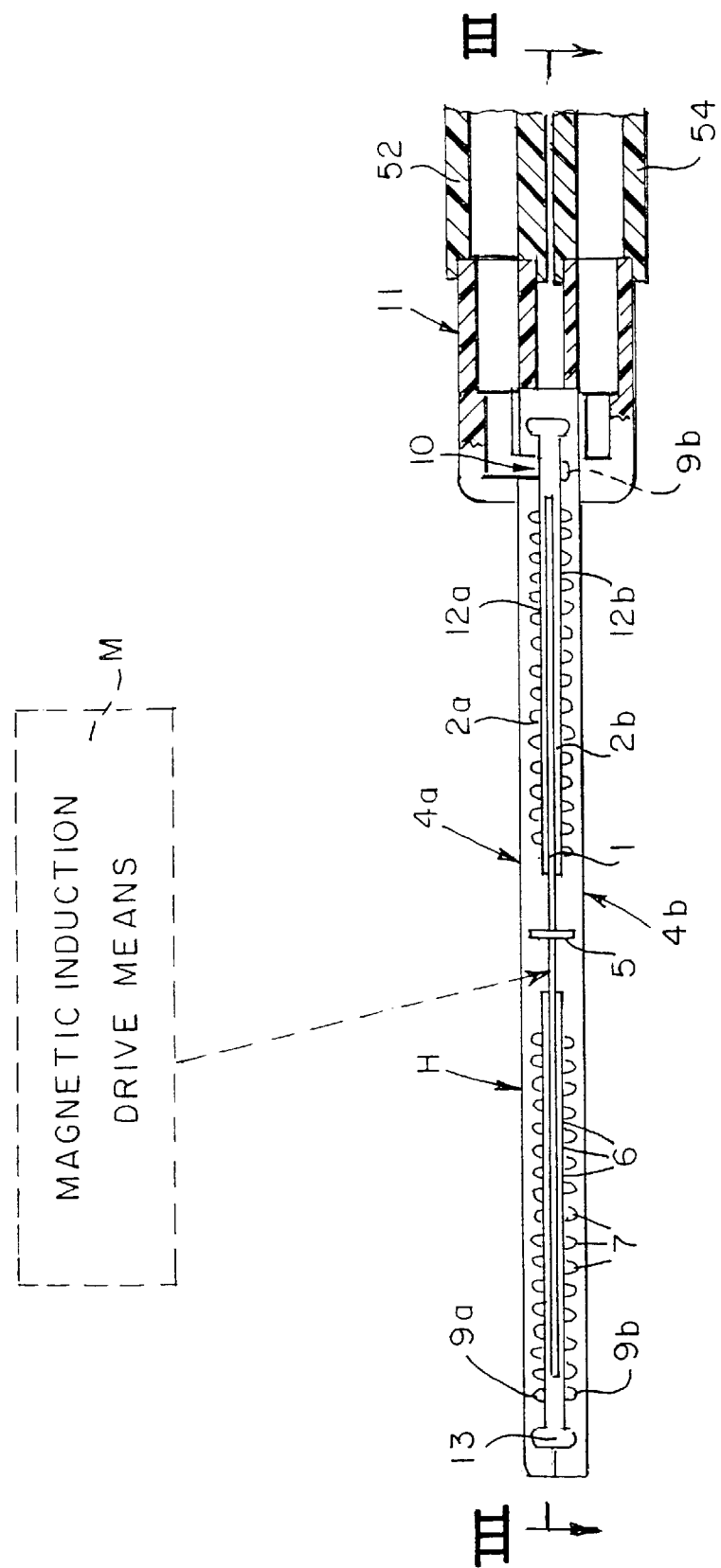
FIG. 2 shows a longitudinal sectional view of an embodiment of the present invention.

A longitudinal section of a filtering device for blood as a further embodiment of the present invention is shown in FIG. 2, which is suitable for plasma separation. The embodiment comprises a housing (H) including two circularly formed, flat half shells 4a, 4b each carrying a membrane 2a and 2b, respectively. A disk 1 is arranged between the membranes 2a, 2b arranged in parallel to one another, said-disk being rotatably supported by a bearing pin 5. Membrane supporting webs 6 and filtrate channels 7 are arranged in a radially direction alternatingly on the side of the respective membranes 2a, 2b opposite the disk 1, wherein the membrane supporting webs 6 are integrally formed in a ring segment-like manner at the half shells 4a 4b by means of injection molding. The half shells 4a, 4b are preferably maid of a transparent acrylic, material.

Figure 3:
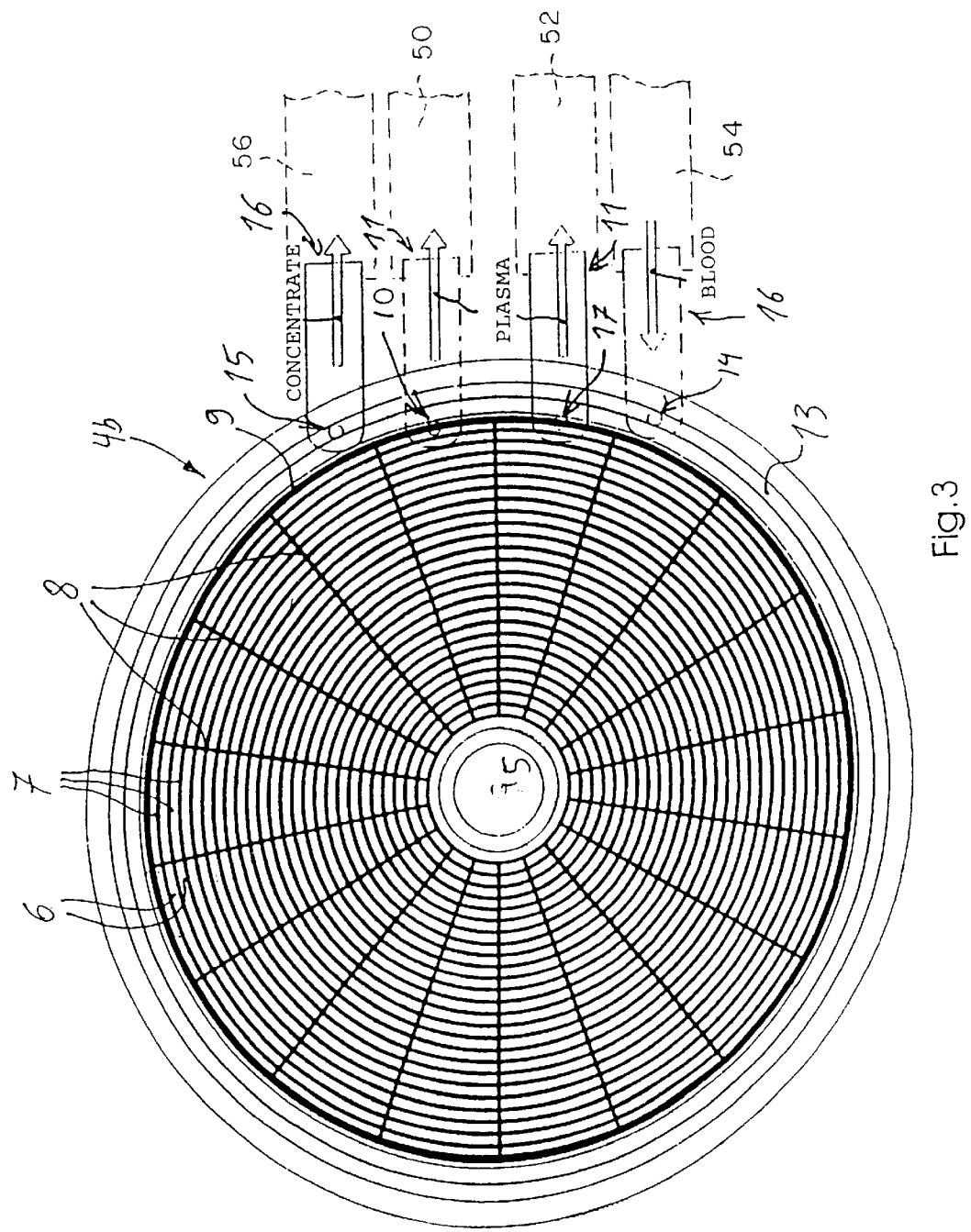
FIG. 3 shows a sectional view along line III—III according to FIG. 2.

As may be derived from the sectional views according to FIGS. 2 and 3, the filtrate channels 7 extend concentrically with respect to thee bearing pin 5 of the disk 2. A plurality of radially extending filtrate discharge channels 8 are provided in the circumferential direction, which open into a filtratering channel 9 annularly arranged around the disk 2. The filtrate channel 9 in turn comprises a filtrate outlet 10, which is provided at the one housing half 4a and leading to the filtrate ring channel 9a provided at this housing half, and a filtrate outlet 17, which is provided in an identical manner at the other housing half 4b and leads to the filtrate ring channel 9b formed at this other housing half. Both filtrate outlets 10, 17 communicate with hose connectors 11a and 11b that are connected with hoses 50 and 52, respectively.

A gap-shaped liquid space 12a, 12b is formed between the respective membranes 2a, 2b and the disk 1. Each gap shaped liquid space 12 communicates with a liquid ring channel 13 radially encompassing the liquid space and communicating therewith. The liquid ring channel 13 comprises a liquid inlet 14 and a concentrate outlet 15. These flow passages 14, 15 are also connected to hose connectors 16a and 16b that are connected with hoses 54 and 56, respectively.

In the embodiment shown, the liquid ring channel 13 has a greater flow cross-section than the gap 12 formed between the two membranes 2a, 2b. The liquid ring channel 13 is formed circularly and arranged concentrically to the bearing pin, wherein the diameter of the liquid ring channel 13 is greater than the diameter of the filtrate ring channel 9.

In the embodiment shown, the he hose connectors 11, 16 are connected to hoses, wherein the hose connected to the liquid outlet can for instance be connected to a dispenser. Blood introduced through the liquid inlet 14 into the two gap-shaped liquid spaces 12a, 12b is first of all guided inwardly as a result of the superposition of shearing force and centrifugal force adjacent to the membrane and in parallel thereto in a helical liquid whirl formed in each of the gap-shaped liquid spaces 12a, 12b. Micro-whirls generated as a result of the shearing force are responsible for the fact that the pores of the membranes 2a, 2b are not clogged in particular by blood corpuscles. In this way along the membrane radially inwardly, the filtration of the blood introduced into the filtering device takes place in a conventional manner as a result of the pressure difference existing at the membrane. In this manner, the filtrate generated is guided via the filtrate channels 7 formed between the membrane half webs 6 into the filtrate is charge channels 8 and is collected though same in the filtrate ring channel 9.

The blood introduced through the liquid inlet 14 into the liquid ring channel 13 is entrained as a result of the rotary motion of the two helical liquid whirls formed in the respective gap-shaped liquid space 12a; 12b between the respective membranes 2a; 2b and the disk 1 with an inwardly directed radial movement component.

The embodiment shown in FIGS. 2 and 3 has the special advantage that it can be used as a disposable article. The two housing halves 4a, 4b are formed in an identical manner, wherein a hose connector 11 to discharge the filtrate (plasma) projecting from the outer front side of the housing half is provided in the present case at each housing half 4a, 4b. Moreover, a further hose connector 16 is provided at each housing half 4a, 4b, said hose connector being used at the one housing half 4b for the discharge of the concentrate and which communicates with the concentrate outlet 15, and at the other housing half 4b for the supply of the unfiltered blood, and which communicates with the liquid inlet 14. By this structure it is possible to manufacture the embodiment for filtering blood as a disposable member essentially consisting of two identically formed injection-molded housing halves 4a, 4b, two membranes 2a, 2b and a disk 1 having bearing pins 5.

A concrete design of the filtering device for blood could for instance be a rotary disk made of V2A steel, which has a thickness of 0.8 mm. The filtering discharge channels 8 can preferably be arranged at a spacing of 20° in the circumferential direction to enable a totally planar discharge of the filtrate i.e. of the separated blood plasma. For a blood filtering device membranes of a cellulose acetate having a pore size of approximately 1 μm are preferably used. The membranes preferably have a diameter of 10 cm and are attached annularly at the outer rim of the respective filtrate channel. The attachment can be made for instance by an adhesive or welded connection. The two housing halves are also joined, wherein this connection can be realized by a welded or adhesive connection. As an alternative, it is also possible to join the two housing halves by means of a latch connection so that the substantially identically formed housing halves merely differ from one another by male and female latch elements. It is, however, essential for the connection of the two housing halves that they are joined in a liquid-tight manner. The two housing halves may for instance be joined in their edge portion by interposition of an annular seal.

The filtering device shown has a thickness of approximately 6 mm, wherein each housing half has a thickness of approximately 2 mm and the filtrate discharge channels 8 and the filtrate channels have a depth of approximately 1 mm. The membranes 2a, 2b have a thickness of approximately 0.1 mm, wherein the spacing between the membranes 2a, 2b and the disk is between 0.4 and 0.6 mm, e.g. 0.5 mm.

In an embodiment dimensioned in accordance with the above dimensions, the filling volume for the filtering device is approximately 10 ml. In case of the filtration of blood, the disk is rotated in this case at a speed of 600 to 1,400, preferably 800 to 1,200 rpm. At such a speed, a sufficiently low shearing force of approximately 10,00 1/s in consideration of a blood damage is generated. The trans-membrane pressure is adjusted to approximately 200 mbar to 300 mbar, preferably to 225 mbar to 275 mbar. In case of these process parameters an average yield of 8 liters plasma at a treatment time of 4 hours at a continuous supply of blood at a flow rate of 100 ml per minute can be achieved.

The features of the device according to the invention and the parameters of the method according to the invention such as material, disk size, surface composition, membrane surface, distance of membrane and disk surface, speed of the disk and trans-membrane pressure substantially depend on the properties of the media to be separated. The filtering device according to the invention and the corresponding method are not restricted to the filtration of blood. Moreover, the filtration in the sense of the invention shall not exclusively be understood as a process in which solid particles are removed from a suspension. Rather, the filtering device according to the invention and the corresponding method can also be applied for instance to separate an emulsion.

As described above, according to a modification of the invention, the shaft 5 can be dispensed with. Rather, the housing is sealed towards the outside in the area of the support of the shaft, so that an emerging, e.g., of toxic liquid, or a penetration of germs or bacterial into the liquid space is safely prevented. A rotary body is especially to be preferred for a contact-less drive said rotary body being metallically conductive so that the drive is effected by means of magnetic induction by means of an outwardly introduced rotating magnetic field by magnetic drive means M. An exchange of used up filtering devices and a coupling with the drive for the rotatably supported rotary body can therefore be carried out in a simple manner.

What is claimed is:

1. A filtering device for removing a filtrate from a liquid, comprising:
    (a) a hollow stationary housing (H) containing a circular thin disk-shaped chamber including a pair of planar parallel spaced side walls, and an outer liquid channel (13) connected between the outer circumferential edges of said chamber side walls;
    (b) a rotatably-driven circular disk (1) arranged concentrically within said chamber;
    (c) a pair of spaced filtering membranes (2a, 2b) arranged within said chamber on opposite sides of said disk, said membranes being spaced from said disk to define a pair of narrow gaps (12a, 12b), respectively, that are in communication with said chamber;
    (d) said housing side walls containing a pair of opposed annular filtrate channels (9a, 9b) arranged in spaced relation concentrically within said outer liquid channel, respectively, said filtrate channels being arranged on opposite sides of said membranes from said gaps, respectively;
    (e) means including first inlet means (14) contained in said housing for supplying the liquid to be filtered to said outer liquid channel;
    (f) means including first outlet means (10, 17) contained in said housing for removing the filtrate from said filtrate channels; and
    (g) means including second outlet means (15) contained in said housing for removing concentrate from said outer liquid channel.

2. A filtering device as defined in claim 1, wherein said housing is sectional and includes a pair of shell sections (4a, 4b) having opposed surfaces that define said chamber side walls, respectively.

3. A filtering device as defined in claim 1, wherein said housing has a greater radial dimension than its axial dimension.

4. A filtering device as defined in claim 1, and further including drive means for driving said disk.

5. A filtering device as defined in claim 4, wherein said housing is formed of a synthetic plastic material; wherein said disk is formed of a conductive material; and further wherein said drive means includes contact-free magnetic induction drive means.

6. A filtering device as defined in claim 1, wherein said chamber side walls contain a plurality of filtering discharge channels (8) extending radially outwardly from the axis of rotation of said disk to said filtrate channel (9), thereby to define between said webs a plurality of arcuate filtrate channels (7) extending between said filtering discharge channels.

7. A method for removing a filtrate from a liquid, comprising:
- (a) introducing the liquid into a space between a rotatably driven member and a stationary filtering membrane;
- (b) establishing a first whirl (3a) in said liquid adjacent said rotatably driven member in a given helical direction in a plane parallel with said rotatably driven member, thereby to produce a radially outwardly directed speed component;
- (c) establishing a second whirl (3b) in said liquid adjacent said stationary filtering membrane in said given helical direction in a plane parallel with said membrane member, thereby to produce a radially inwardly directed speed component; and
- (d) passing the liquid through the membrane; thereby to separate the filtrate from the liquid.

8. A method for removing a filtrate from a liquid as defined in claim 7, wherein said liquid space is defined by a chamber in a synthetic plastic housing; and wherein said movable member is formed of a conductive material and is rotated in a contact-free manner by magnetic inductive field means.

* * * * *